United States Patent
Moszner et al.

(10) Patent No.: US 12,357,287 B2
(45) Date of Patent: Jul. 15, 2025

(54) OCCLUSION DEVICE AND METHOD FOR ITS MANUFACTURE

(71) Applicant: Occlutech GmbH, Jena (DE)

(72) Inventors: Robert Moszner, Bad-Klosterlausnitz (DE); Hans-Reiner Figulla, Jena (DE); Friedrich Moszner, Hohlstedt (DE); Florian Krizanic, Jena (DE)

(73) Assignee: Occlutech GmbH, Jena (DE)

( * ) Notice: Subject to any disclaimer, the term of this patent is extended or adjusted under 35 U.S.C. 154(b) by 0 days.

(21) Appl. No.: 18/364,432

(22) Filed: Aug. 2, 2023

(65) Prior Publication Data
US 2024/0016488 A1    Jan. 18, 2024

Related U.S. Application Data

(63) Continuation of application No. 16/745,209, filed on Jan. 16, 2020, now Pat. No. 11,751,858, which is a
(Continued)

(30) Foreign Application Priority Data

Mar. 24, 2006 (DE) .......................... 102006013770.1

(51) Int. Cl.
*D04C 1/06* (2006.01)
*A61B 17/00* (2006.01)
(Continued)

(52) U.S. Cl.
CPC .... *A61B 17/0057* (2013.01); *A61B 17/12109* (2013.01); *A61B 17/12122* (2013.01);
(Continued)

(58) Field of Classification Search
CPC .................................. D04C 3/48; D04C 1/06
See application file for complete search history.

(56) References Cited

U.S. PATENT DOCUMENTS

| | | |
|---|---|---|
| 4,336,809 A | 6/1982 | Clark |
| 4,538,609 A | 9/1985 | Takenaka et al. |
| (Continued) | | |

FOREIGN PATENT DOCUMENTS

| | | |
|---|---|---|
| CN | 2524710 Y | 12/2002 |
| CN | 2613248 Y | 4/2004 |
| (Continued) | | |

OTHER PUBLICATIONS

AGA Medical Corporation, "Expert Witness Report regarding: Occlutech GmbH and AGA Medical Corporation and Dot Medical Limited" prepared by William J. Drasler, BS, MS, PhD., Feb. 8, 2009, 54 pages.

*Primary Examiner* — Bao-Thieu L Nguyen
(74) *Attorney, Agent, or Firm* — Inskeep IP Group, Inc.

(57) ABSTRACT

The present invention relates to an occlusion device (1) consisting of a braiding (2) of thin wires or threads (4) which is given a suitable form in a molding and heat treatment procedure. The occlusion device (1) has a proximal retention area (6) and a distal retention area (8), whereby the ends of the wires or threads (4) converge into a holder (5) in distal retention area (8). A cylindrical crosspiece (10) is furthermore disposed between the proximal and distal retention areas (6, 8). With the objective of providing an occlusion device which positions as flat as possible against the septum at the proximal side of a septal defect in the inserted state, the invention provides for the proximal retention area (6) of the braiding (2) to exhibit a completely closed proximal wall (112) disposed with a continuous surface at the proximal end of the occlusion device (1) which forms the proximal end (12) of said occlusion device (1).

3 Claims, 10 Drawing Sheets

Related U.S. Application Data continuation of application No. 15/357,394, filed on Nov. 21, 2016, now Pat. No. 10,743,852, which is a continuation of application No. 12/843,788, filed on Jul. 26, 2010, now Pat. No. 9,532,772, which is a continuation of application No. 11/689,550, filed on Mar. 22, 2007, now abandoned.

(51) Int. Cl.
  *A61B 17/12* (2006.01)
  *D04C 3/48* (2006.01)

(52) U.S. Cl.
  CPC .......... *A61B 17/12172* (2013.01); *D04C 1/06* (2013.01); *D04C 3/48* (2013.01); *A61B 2017/00004* (2013.01); *A61B 2017/00526* (2013.01); *A61B 2017/00575* (2013.01); *A61B 2017/00592* (2013.01); *A61B 2017/00606* (2013.01); *A61B 2017/00615* (2013.01); *A61B 2017/00623* (2013.01); *A61B 2017/00867* (2013.01); *A61B 17/12022* (2013.01); *D10B 2509/08* (2013.01)

(56) References Cited

U.S. PATENT DOCUMENTS

| | | | |
|---|---|---|---|
| 4,624,243 A | 11/1986 | Lowery et al. | |
| 4,704,918 A * | 11/1987 | Orkin | F16C 7/026 464/181 |
| 4,722,337 A | 2/1988 | Losch et al. | |
| 4,744,624 A | 5/1988 | Burston | |
| 5,007,704 A | 4/1991 | McCartney | |
| 5,125,058 A | 6/1992 | Tenerz et al. | |
| 5,304,171 A | 4/1994 | Gregory et al. | |
| 5,341,758 A * | 8/1994 | Strickland | B63B 34/60 87/6 |
| 5,362,344 A * | 11/1994 | Ben-Porat | D04C 3/48 416/241 A |
| 5,540,678 A | 7/1996 | Long et al. | |
| 5,645,559 A * | 7/1997 | Hachtman | D04C 3/48 606/198 |
| 5,725,552 A | 3/1998 | Kotula et al. | |
| 5,825,958 A | 10/1998 | Gollihar et al. | |
| 5,846,261 A | 12/1998 | Kotula et al. | |
| 5,944,738 A | 8/1999 | Amplatz et al. | |
| 5,949,929 A | 9/1999 | Hamm | |
| 5,957,974 A * | 9/1999 | Thompson | A61F 2/07 623/1.53 |
| 6,086,577 A | 7/2000 | Ken et al. | |
| 6,095,970 A | 8/2000 | Hidaka et al. | |
| 6,214,029 B1 | 4/2001 | Thill et al. | |
| 6,221,086 B1 | 4/2001 | Forber | |
| 6,334,864 B1 | 1/2002 | Amplatz et al. | |
| 6,346,117 B1 | 2/2002 | Greenhalgh | |
| 6,439,099 B1 * | 8/2002 | Carlson | F42B 3/087 102/275.12 |
| 6,468,303 B1 | 10/2002 | Amplatz et al. | |
| 6,475,227 B2 | 11/2002 | Burke et al. | |
| 6,506,204 B2 * | 1/2003 | Mazzocchi | A61B 17/12022 606/213 |
| 6,626,939 B1 * | 9/2003 | Burnside | D04C 1/06 623/1.53 |
| 6,964,674 B1 | 11/2005 | Matsuura et al. | |
| 9,532,772 B2 * | 1/2017 | Moszner | A61B 17/12109 |
| 9,826,980 B2 | 11/2017 | Figulla et al. | |
| 10,743,852 B2 * | 8/2020 | Moszner | A61B 17/12172 |
| 11,751,858 B2 * | 9/2023 | Moszner | A61B 17/0057 606/213 |
| 2001/0015510 A1 * | 8/2001 | Nakamura | D04C 3/48 264/159 |
| 2003/0083735 A1 | 5/2003 | Denardo et al. | |
| 2003/0199923 A1 * | 10/2003 | Khairkhahan | A61F 2/0108 606/213 |
| 2004/0172056 A1 | 9/2004 | Guterman et al. | |
| 2005/0228434 A1 * | 10/2005 | Amplatz | A61B 17/12122 606/200 |
| 2005/0267556 A1 * | 12/2005 | Shuros | A61P 9/10 607/9 |
| 2005/0288764 A1 * | 12/2005 | Snow | A61F 2/966 623/1.11 |
| 2006/0224183 A1 * | 10/2006 | Freudenthal | A61B 17/12031 606/213 |
| 2007/0043391 A1 * | 2/2007 | Moszner | D04C 3/40 606/213 |
| 2007/0112381 A1 * | 5/2007 | Figulla | A61B 17/0057 606/213 |
| 2007/0225760 A1 * | 9/2007 | Moszner | D04C 3/48 606/213 |

FOREIGN PATENT DOCUMENTS

| | | |
|---|---|---|
| CN | 1736346 A | 2/2006 |
| EP | 0 280 397 A2 | 8/1988 |
| GB | 2 352 922 A | 2/2001 |
| WO | WO 1993/014432 A2 | 7/1993 |
| WO | WO 1998/047430 A1 | 10/1998 |
| WO | WO 1999/012478 A1 | 3/1999 |
| WO | WO 2004/012589 A2 | 2/2004 |
| WO | WO 2004/064671 A2 | 8/2004 |
| WO | WO 2005/020822 A1 | 3/2005 |

* cited by examiner

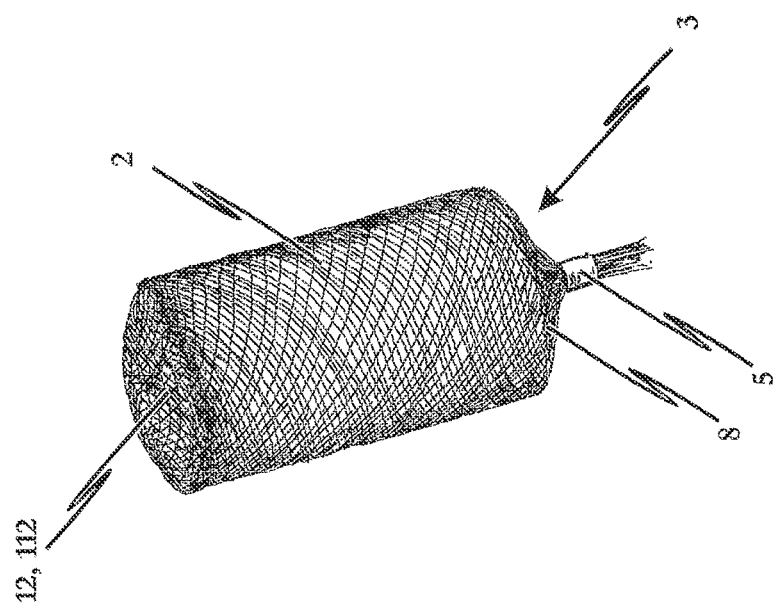
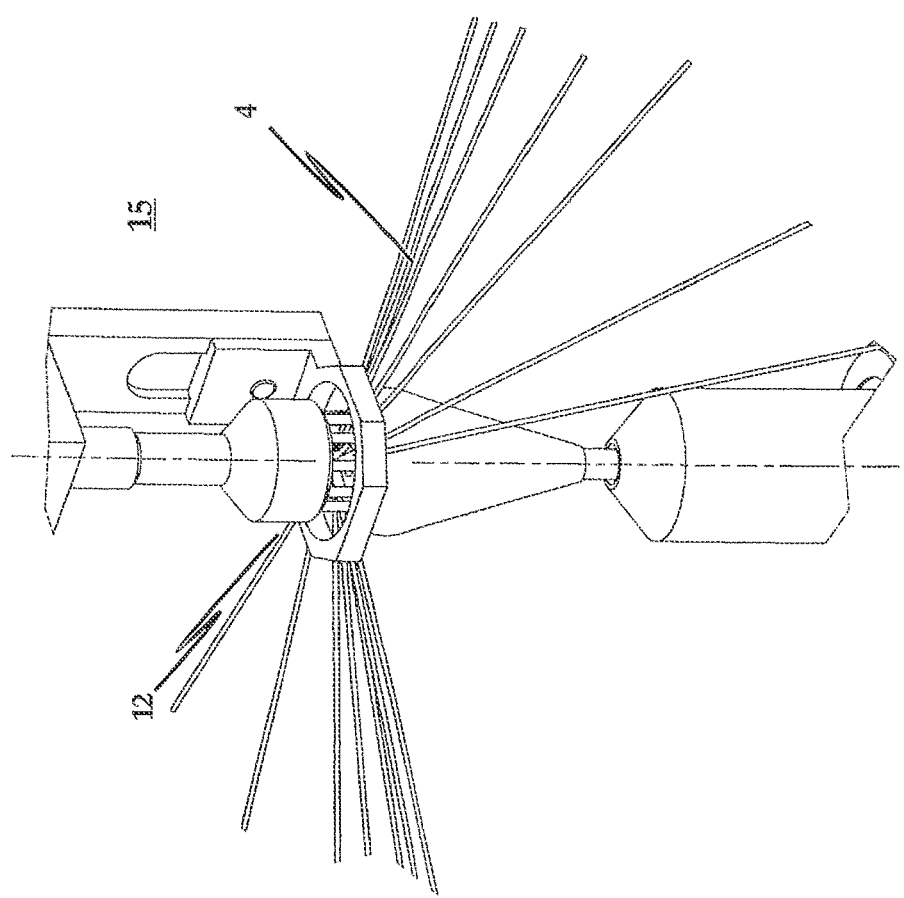
Fig. 7
Fig. 6

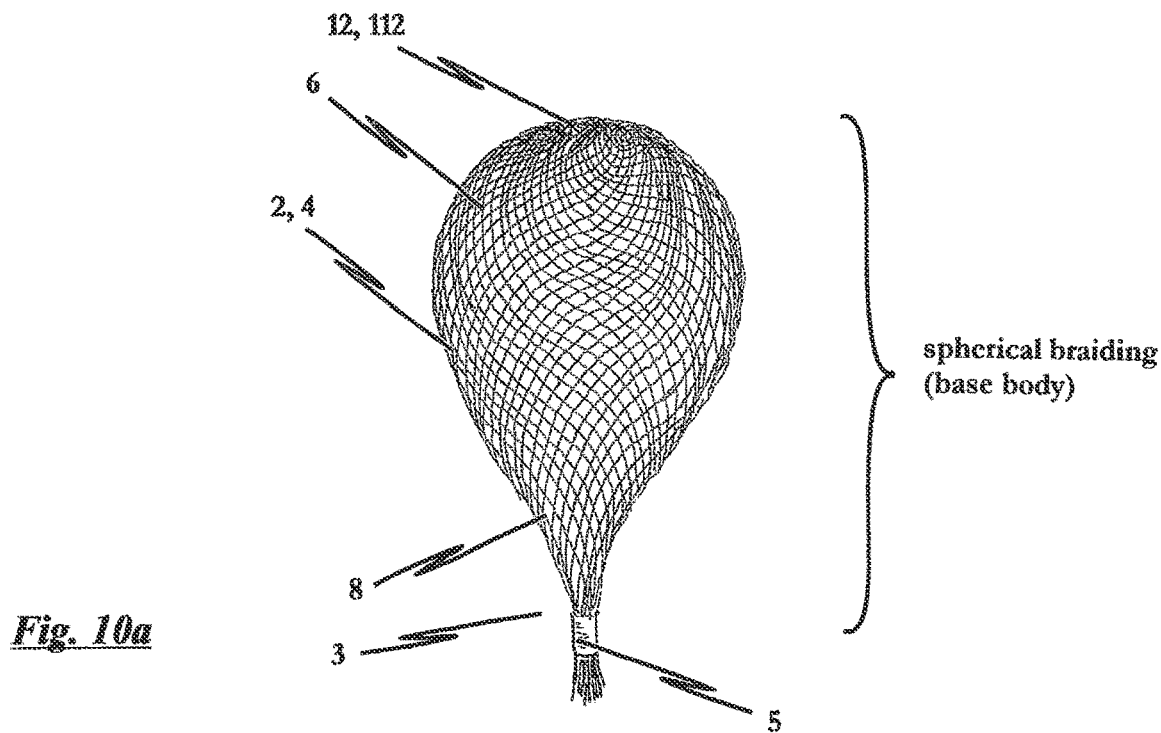
*Fig. 10a* — spherical braiding (base body)
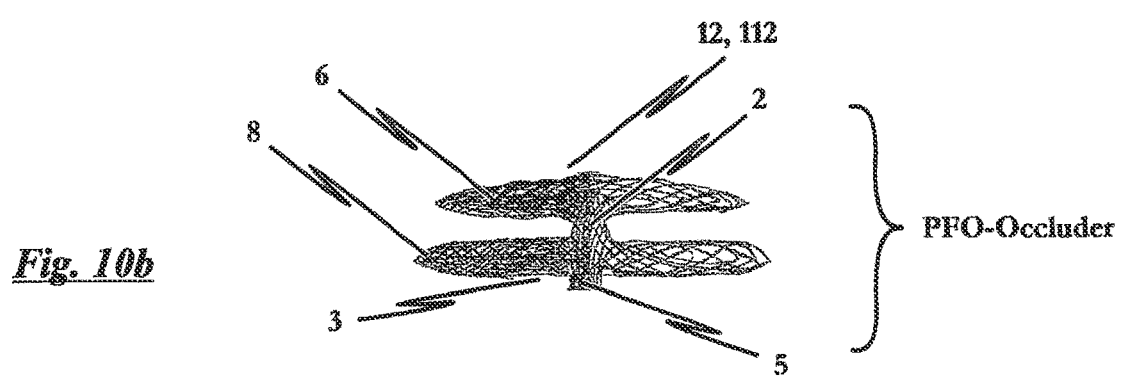
*Fig. 10b* — PFO-Occluder
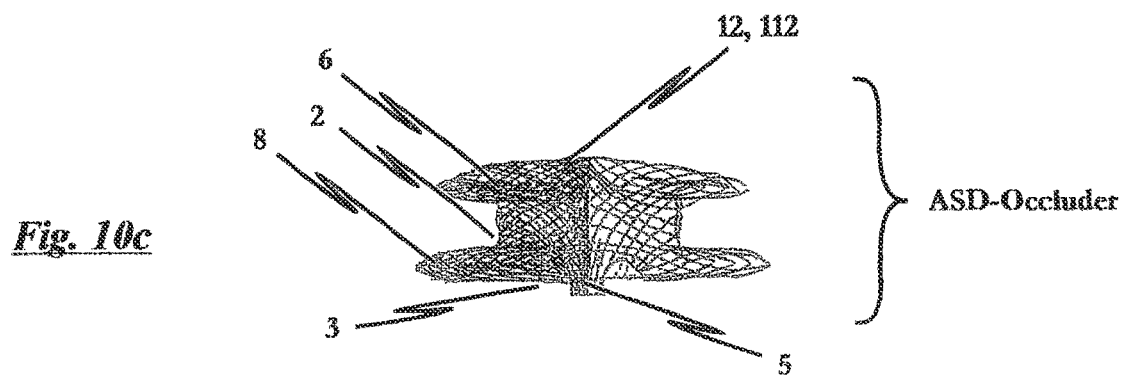
*Fig. 10c* — ASD-Occluder

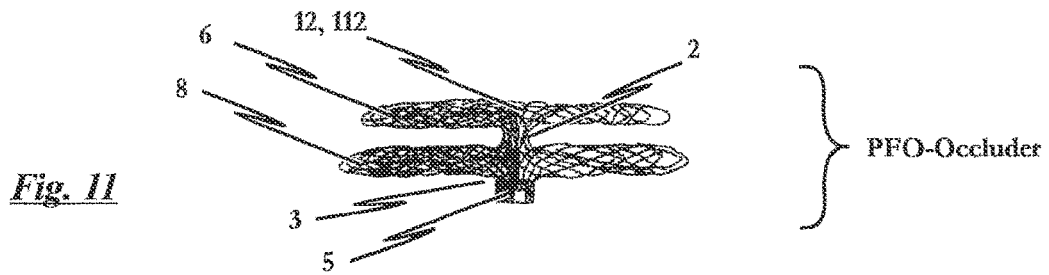
*Fig. 11* — PFO-Occluder
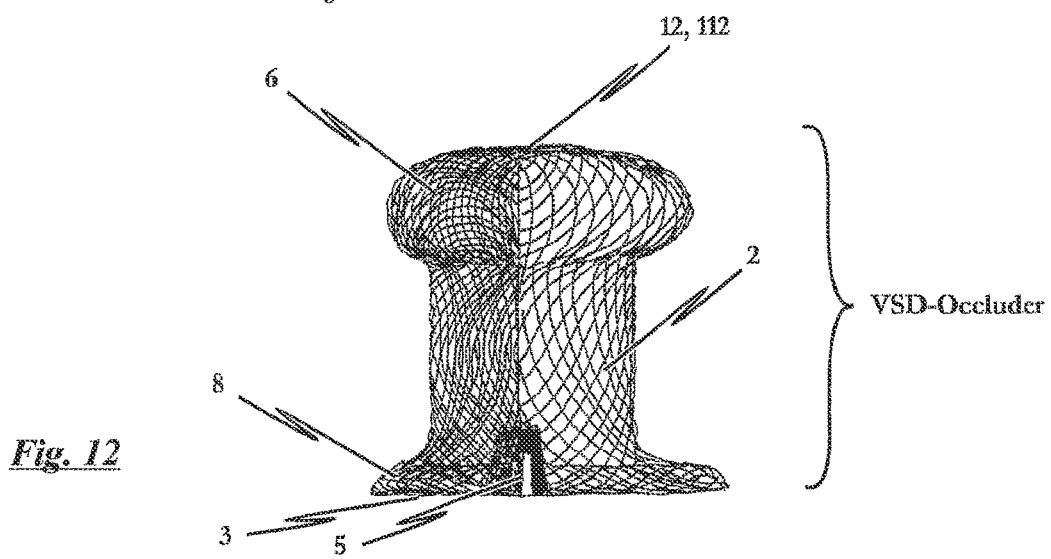
*Fig. 12* — VSD-Occluder
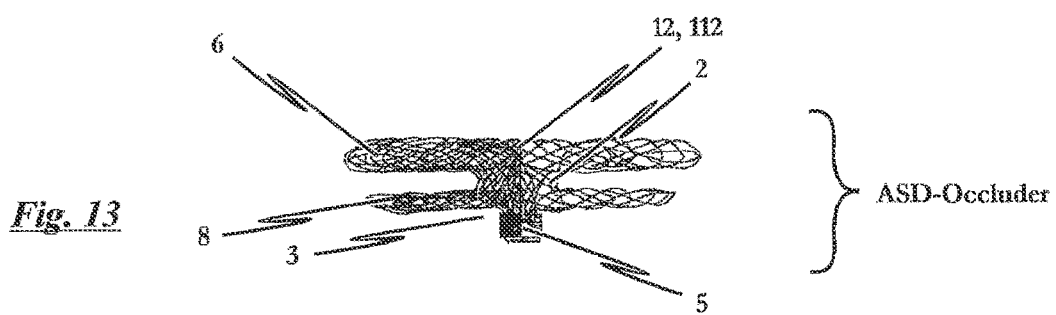
*Fig. 13* — ASD-Occluder
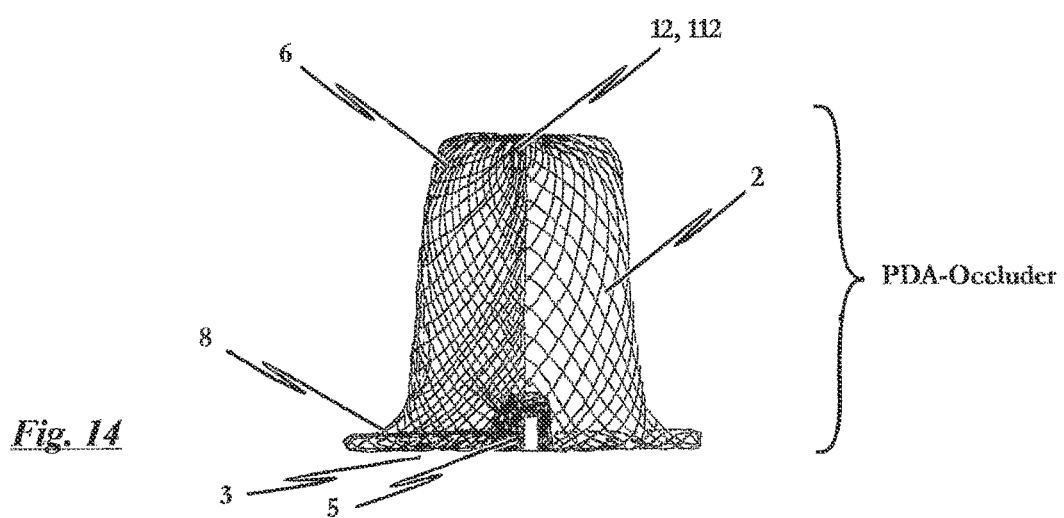
*Fig. 14* — PDA-Occluder

OCCLUSION DEVICE AND METHOD FOR ITS MANUFACTURE

RELATED APPLICATIONS

The present application is a continuation of and claims priority to U.S. patent application Ser. No. 16/745,209 filed Jan. 16, 2020 entitled Occlusion Device And Method For Its Manufacture; which is a continuation of and claims priority to U.S. patent application Ser. No. 15/357,394 filed Nov. 21, 2016 entitled Occlusion Device And Method For Its Manufacture (now U.S. Pat. No. 10,743,852 issued Aug. 18, 2020); which is a continuation of and claims priority to U.S. patent application Ser. No. 12/843,788 filed Jul. 26, 2010 entitled Occlusion Device And Method For Its Manufacture (now U.S. Pat. No. 9,532,772 issued Jan. 3, 2017); which is a continuation of U.S. patent application Ser. No. 11/689,550 filed Mar. 22, 2007 entitled Occlusion Device And Method For Its Manufacture (now abandoned); which claims benefit of German Patent Application No. 10 2006 013 770.1, filed Mar. 24, 2006 entitled Occlusions instrument and Varfahren zu dessen Herstellung; all of which are hereby incorporated herein by reference in their entireties.

FIELD OF THE INVENTION

The present invention relates to an occlusion device consisting of a holder and a braiding of thin wires or threads given a suitable form by means of a molding and heat treatment procedure, whereby the occlusion device has a proximal retention area and a distal retention area, wherein the ends of the wires converge into a holder in the distal retention area, and a cylindrical crosspiece interposed between the proximal and distal retention areas, whereby the two retention areas are positioned on the two sides of a shunt to be occluded in a septum, usually by way of an intravascular surgical procedure, while the crosspiece transverses the shunt. The invention moreover relates to a method for manufacturing said occlusion device.

BACKGROUND OF THE INVENTION

Medical technology has long endeavored to be able to occlude septal defects, for instance atrial septal defects, with non-surgical transvenous catheter intervention, in other words, without having to perform an operation in the literal sense. Various different occlusion systems have been proposed, each with their own advantages and disadvantages, without any one specific occlusion system having yet become widely accepted. In making reference to these different systems, the following will use the terms "occluder" or "occlusion device."

In all interventional occlusion systems, a self-expanding umbrella system is introduced transvenously into a defect to be occluded in a septum. This type of system might comprise two umbrellas; one positioned at the distal side of the septum, for example the side farthest from the median plane of the body/heart), and one at the proximal side of the septum (i.e. the side closer to the median plane of the body), whereby the two umbrella prostheses are subsequently fitted into a double umbrella in the septal defect. Thus, in the assembled state, the occlusion system usually consists of two fixed umbrellas connected to one another by means of a short peg which passes through the defect.

However, a disadvantage to such known prior art occlusion devices turns out to be the relatively complicated, difficult and complex implantation procedure. Apart from the complicated implantation of the occlusion system in the septal defect to be occluded, the umbrellas utilized are fundamentally susceptible to material fatigue along with fragment fracture. Furthermore, thromboembolic complications are frequently to be anticipated.

With another type of occlusion device, the so-called Lock-Clamshell umbrella system, two stainless steel, preferably Dacron-covered, umbrellas are provided, each stabilized by four arms. This type of occluder is implanted into the patient through a vein. However, seen as problematic with the Lock-Clamshell occluder is the fact that the insertion instruments necessary to implant the device need to be of relatively large size. A further disadvantage is that many different occluder sizes are needed in order to cope with the respective proportions of the septal defects to be occluded. It thus turns out that the umbrellas do not flatten out completely in the inserted state if the length or the diameter of the crosspiece inserted into the defect is not of an optimum match. This results in incomplete endothelialization. It has furthermore been shown that over a longer period of time, many of the systems implanted into patients' bodies will exhibit material fatigue and fractures in the metallic structures due to the substantial mechanical stresses. This is especially the case given permanent tension between an implant and the septum.

In order to overcome these disadvantages, self-centering occlusion devices have been developed which are inserted into the body of the patient and introduced into the septal defect to be occluded by way of a minimally-invasive procedure, for example using a catheter and guide wires. Their design is based on the principle that the occlusion device can be tapered to the dimensions of the insertion instrument and/or catheter used for the intravascular surgical procedure. Such a tapered occlusion device is then introduced by catheter into the septal defect to be occluded, respectively into the shunt of the septum defect to be occluded. The occluder is then discharged from the catheter, upon which the self-expanding umbrellas, retention discs respectively, subsequently unfold against the two sides of the septum. The umbrellas in turn comprise fabric inserts made from or covered by, for example, Dacron, with which the defect/shunt is occluded. After a few weeks or months, the body's own tissue more or less completely envelops the implants remaining in the body.

An example of this type of self-centering occlusion device is known from U.S. Pat. No. 5,725,552, which describes an occlusion device known as the "Amplatz occluder." This known system will be briefly described below with reference to FIGS. 15a to 15c. Specifically, FIG. 15a shows a tubular braiding known from the prior art, for example said U.S. Pat. No. 5,725,552, as the base structure or starting body for manufacturing this type of known occlusion device, whereby each end of the tubular braiding needs to be held in a respective holder. FIG. 15b depicts a side sectional view of the right side of a known PFO-type occlusion device from the prior art, for example said U.S. Pat. No. 5,725,552, with the occlusion device being made from a tubular braiding in accordance with FIG. 15a, while FIG. 15c shows a right-side sectional view of a further ASD-type occlusion device likewise known from U.S. Pat. No. 5,725,552, with this occlusion device also being made from a tubular braiding in accordance with FIG. 15a.

To be understood by the term "PFO-type" as used herein is an occlusion device for treating a patent foramen ovale (PFO) while the term "ASD-type occlusion device" refers to an occlusion device for treating atrial septal defects.

The known occlusion devices consist of a braiding of a plurality of fine, intertwined nitinol wire strands in the shape of a yo-yo. Each braiding is manufactured in its initial form as a rounded braiding having loose wire ends both at its leading end (its proximal side, respectively) as well as at its trailing end (its distal side, respectively). During the subsequent processing of the rounded braiding, these loose ends must then be gathered into a collar and welded together. After the appropriate processing, both the proximal side as well as the distal side of the finished occluder exhibit a protruding collar. Dacron patches are sewn into the distal and proximal retention umbrellas and the interposed crosspiece. Because of the memory effect of the nitinol material used, the two retention umbrellas unfold by themselves upon exiting the catheter, initially in a balloon-like intermediate stage, whereby the retention umbrellas ultimately positioned on the two sides of the septum eventually assume a more or less flattened form. The crosspiece centers itself automatically into the shunt to be occluded as the umbrellas expand.

Because the collar protrudes past the proximal retention area of the occluder, the problem arises that the inserted implant causes embolic-related problems, in particular consecutive embolization. Because portions of the occlusion device protrude past the septum wall and are in continuous contact with the blood, defense system reactions are also a frequent occurrence. Furthermore, a complete endothelialization of the occluder implant is often prevented.

An occlusion device of the type indicated at the outset as well as a method for manufacturing such an occlusion device is additionally known from WO 2005/020822 A1. The occlusion device described therein essentially consists of a braiding of thin wires or threads made from a material having shape-memory function. In the expanded state, the known occlusion device exhibits a proximal and a distal retention area as well as a cylindrical crosspiece interposed between the two.

Because the proximal retention area of the braiding exhibits a form which is open to the proximal end in this prior art, it basically allows the rim of the proximal retention area to lie flat against the septal wall when the occlusion device is in the inserted state while the retention area does not protrude beyond the septal wall.

The manufacturing process according to WO 2005/020822 A1 utilizes a braiding technique which forms a tubular braiding open to the top, which need only be provided with a holder for bundling the braiding's threads or wires on one end, while at the opposite end, the braiding's threads or wires are intertwined from their center. It thus becomes possible to produce a braiding to serve as the base structure for the known occlusion device, whereby the proximal retention area of the base structure exhibits a form open to the proximal end.

To further define the occlusion device known from WO 2005/020822 A1 more specifically, particular reference is made to FIGS. 16a to 16c. In detail, FIG. 16a shows a tulip or bell-shaped braiding having a distal holder known, for example, from WO 2005/020822 A1. FIG. 16b depicts a sectional view of the right side of a PFO-type occlusion device known from WO 2005/020822 A1, whereby the occlusion device is made from a tubular braiding in accordance with FIG. 16a. FIG. 16c finally shows another sectional view of the right side of an ASD-type occlusion device known from WO 2005/020822 A1, with the occlusion device likewise being made from a tubular braiding in accordance with FIG. 16a.

In the case of these occlusion devices known from WO 2005/020822 A1, it has proven disadvantageous for the braiding on the proximal end to exhibit an opening which needs to be spanned by, for example, a Dacron insert or a cloth so that the finished occlusion device will no longer be open at its proximal end. Producing such an occlusion device necessitates quite a complex manufacturing process, and one which is thereby cost-intensive. Furthermore, different materials, namely the materials of the braiding and of the Dacron insert or cloth need to be force-fit to one another. Such joints are inherent weak points in terms of material fatigue. Thus, this known type of occluder has an increased risk of material fatigue along with fragment fracture. It has furthermore been shown that such an implanted system can exhibit material fatigue and fractures in the joints between the metallic structures and the Dacron insert after a longer period of time within a patient's body, stemming from the considerable mechanical stresses. This is especially the case when there is permanent tension between the braiding and the insert.

Moreover, thromboembolic complications need to be considered with the occlusion devices known from WO 2005/020822 A1. While the known system enables the rim of the proximal retention area to lie flat against the septal wall and not have the retention area project beyond the septal wall when the occlusion device is in the inserted state, the proximal end of the known occlusion device nevertheless exhibits a manufacturing-contingent opening at the proximal wall axial to the crosspiece. Even if this opening is—as described above—closed with a Dacron insert, for example, the known system cannot prevent the finished occlusion device from having at least one remaining trough-shaped recess or sometimes even components protruding in the proximal retention area of the occluder, these being at the very location where the opening closed with the Dacron insert is disposed.

Along with trough-shaped recesses and protruding components comes yet another problem, that of the inserted implant causing embolic-related problems, in particular consecutive embolization. These embolic-related problems arise especially when the patient is suffering from so-called atrial fibrillation of the heart. This is a condition in which frequent excitation of the heart's upper chambers results in their not contracting. As a consequence of the left and right halves of the heart being deprived of contraction, the blood is ineffectively swirled and mixed and thrombi can form in the atrium. A considerable risk when atrial fibrillation causes thrombi to form in the atrium is that these thrombi can be carried along in the bloodstream and enter the arterial circulation. Apoplectic strokes, occurring in approximately 5% of atrial fibrillation patients each year, are a particular consequence of this embolization when not chronically treated with so called dicumerol, a blood anticoagulant. However, anticoagulating the blood with so called dicumerol is also not without risks. One side effect of dicumerol treatment is increased bleeding such that there are contraindications for this treatment for approximately 20% of all atrial fibrillation patients and the patients thus have to hazard the risk of a stroke when weighing the bleeding/stroke risk.

The present invention therefore addresses the problem of refining such an occlusion device as known to medical technology and described in WO 2005/020822 A1 so as to overcome the disadvantages cited above. A particular objective is the providing of an occlusion device applicable to occluding defects of different sizes, whereby implantation of the occluder is to be a simple procedure. Furthermore, the occurrence of such usual occluder complications such as dislocation, partial embolization or occluder material fatigue is to be reduced to the greatest extent possible. Above and beyond that, an occlusion device is to be provided which ensures occlusion of a septal defect with as few portions of the occlusion device as possible protruding past the septum wall so as to avoid the associated and above-cited complications.

OBJECTS AND SUMMARY OF THE INVENTION

Based on the problem as posed and starting out from the system as known from WO 2005/020822 A1, it is the task of the present invention to provide an occlusion device which lies as flat as possible against the septum in the inserted state at the proximal side of the septal defect, and with which the risk of material fatigue with fragment fracture is considerably reduced, and to do so at a lower manufacturing cost. The present invention moreover has the technical task of providing a method for manufacturing such an occlusion device.

These tasks are solved in accordance with the invention by an occlusion device of the type specified at the outset having the proximal retention area of the braiding exhibit a completely closed proximal wall at the proximal end of the occlusion device with a continuous surface forming the proximal end of the occlusion device.

The problem of process-engineering the present invention is furthermore solved by a method for manufacturing the above-cited occlusion device which is characterized by the process step of forming a ball-shaped, bulb-shaped or teardrop-shaped hollow braiding by means of a braiding process known per se and by the process step of forming a proximal retention area and a distal retention area at the bundled first end, and interposing a cylindrical crosspiece between said proximal and distal retention areas. It is thereby provided for the hollow braiding to be bundled at a first distal end and to exhibit a completely closed proximal wall having a continuous surface on an opposite second proximal end.

To be understood by the term "proximal wall" as used herein is that segment or region of the proximal retention area of the braiding at the proximal end of the occlusion device which forms the closure for the defect to be occluded on the proximal end.

The particular advantages of the invention lie in providing an intravascular occlusion device, especially for the treatment of septal defects, whereby the occluding device is suited to be administered by catheter to the defect to be occluded. Because the proximal retention area of the braiding has a fully closed proximal wall at the proximal end which exhibits a continuous surface forming the proximal end of the occlusion device, a particular advantage afforded by the occlusion device—independent of the diameter size to the defect to be occluded and independent of the septal wall's thickness—is in its self-adjusting to the defect in the septal wall and doing so specifically that no portion of the occlusion device protrudes into the plane of the septal wall having the defect on the proximal side of the defect. In the inventive solution, this plane; i.e., the plane of the septal wall with the defect, is formed by the fully closed proximal wall of the occlusion device. On the other hand, the inventive solution ensures that this proximal wall will contain no recesses or other "discontinuities" in the mathematical sense such as sharp edges, kinks, etc. whatsoever, so that the usual associated complications, in particular as regards embolic-related problems, can no longer occur.

Above all to be achieved is that the inserted occlusion device will be fully enveloped by the body's own tissue substantially faster than is the case with the occluding systems known in the prior art. The further advantage of better mechanical stability over the long term compared to the systems known in the prior art is a function derived from using a braiding made of thin wires or threads as the starting material for the inventive occlusion device. This largely prevents fractures from occurring in the structure of the inserted implant. The braiding furthermore has a better rigidity since the entire structure is made from one material and without any connecting joints.

Especially due to the inventive solution being able to completely dispense with fabric or Dacron inserts, as is the case for example with the occluder system pursuant WO 2005/020822 A, the premature development of material fatigue can be effectively further reduced, whereby even the overall manufacturing costs can be additionally lowered.

The fully closed proximal wall provided at the proximal retention area of the braiding additionally allows the proximal retention area of the device to flatten completely against the lateral edge of the defect in the inserted state and to specifically do so virtually independently of the diameter to the defect or the thickness of the septal wall. As a result, the occlusion device can be used for a wide range of differently-sized septal defects. Because there is then no need for a holder for the bundled or gathered braiding at the proximal retention area, there are also no components of the occlusion device to protrude beyond the septal wall which prevents the components of the implant from being in continuous contact with the blood. This yields the advantage of there being no threat of the body mounting any defense mechanism reactions or of there being any thromboembolic complications.

The inventive method affords the prospect of realizing a particularly simple manufacturing of the occlusion device described above. First, a ball-shaped, bulb-shaped or teardrop-shaped hollow braiding is formed, for example using a round braiding machine. The technology used here is one in which the configured braiding is bundled at the trailing end of the length of the braiding; i.e., at what will later be the distal end of the occlusion device, while the leading end of the length of the braiding; i.e., what will later be the proximal end of the occlusion device, is closed. It is thereby possible to manufacture a "bag-shaped" hollow braiding, the bundled end of which corresponds to the distal end of the finished occlusion device and its opposite closed end the proximal end or the proximal wall of the finished occlusion device. Because a known braiding method is used to produce the occlusion device, the finished occlusion device exhibits mechanical properties in terms of, for example, expansion, stability, strength, etc., which can be custom-adapted to the later use of the occlusion device. In advantageous manner, metallic wires or even organic threads can be incorporated into the braiding. It goes without saying that the terms as used herein of "ball-shaped," "bulb-shaped," "teardrop-shaped" and "bag-shaped" are to respectively refer to forms which have shapes comparable to a ball, a bulb, a teardrop or a bag. The invention is in particular not limited solely to an exact spherical shape, etc.

With respect to the occlusion device itself, preferred embodiments of the invention are specified in subclaims 2 to 10 and, with respect to the manufacturing process, in subclaims 12 and 13.

It is particularly preferred for the proximal wall of the occlusion device to exhibit a curved surface as the continuous surface. It is hereby essential that the curvature to this surface have no discontinuities such as, for example, edges, corners, etc. With respect to the term "continuity" as used herein, this refers to the mathematical definition of a continuous surface as known in the field of topology. For example, it would be conceivable for the proximal wall to exhibit a curved surface which in respect to the plane of the septal wall with the defect, has a preferably slightly concave curve so as to ensure a particularly good, i.e. flat and even fitting of the proximal wall against the septal wall. It is of course also conceivable that the surface of the proximal wall be preferably configured to be slightly convex relative the septal wall, this thereby achieving that the force-fit connection between the proximal wall, the peripheral area of the proximal wall respectively, and the septal wall at the defect to be occluded is particularly large so as to thus enable a better anchorage for the occlusion device in the defect to be occluded. It would also be conceivable for the outer region of the proximal wall to be formed with a slight concave which transitions into a convex form toward the middle; i.e. toward the position axial to the crosspiece of the occlusion device. This can also yield advantages, especially as regards anchoring the occlusion device in the defect to be occluded.

A particularly preferred realization of the latter embodiment in which the proximal wall of the occlusion device exhibits a curved surface as the continuous surface provides for the curved surface to conform to the surface of a section of a ball-shaped, bulb-shaped or teardrop-like body. In other words, this means that the proximal wall of the occlusion device can be configured in the shape of a spherical cap or a segment of a teardrop, for example. Of course, other profiles are just as conceivable here. Of particular advantage is that the inventive solution basically allows for the optimum use of an occlusion device independent of the type and in particular of the size of the defect to be occluded.

It is of particular preference for the occlusion device to have the braiding consist of nitinol or of another shape-memory material or material having memory effect. Such other material could conceivably be, for example, copper-zinc-aluminum alloys, gold cadmium alloys or even ferrous alloys such as e.g. iron-manganese-silicon alloys, or also plastics, all of which are characterized by their extremely high memory capacity.

It is particularly preferably provided for the braiding of the inventive occlusion device to be formed from a shape-memory polymer based on, for example, a polyanhydride matrix or on a polyhydroxycarboxylic acid. These are synthetic degradable materials which have a thermally-induced shape-memory effect. Yet also conceivable would be other shape-memory polymers such as, for example, block copolymers as described for example in the special edition of Angewandte Chemiel 2002, 114, pages 2138 to 2162, by A. Lendlein and S. Kelch.

By making use of such a material, it is possible to utilize a bag-shaped hollow braiding which is closed at its one end and open and bundled at its other end for the starting body of the occlusion device, produced for example in a round braiding method. Said starting body is then subsequently brought into the desired form for the occlusion device by means of a molding and heat treatment procedure. Other treatment procedures are of course also conceivable here.

An advantageous further development of the latter described embodiment of the inventive occlusion device in which the braiding is made from a shape-memory material provides for the material to be a biodegradable shape-memory polymer material. Synthetic biodegradable implant material is particularly suitable. Such degradable materials or polymers contain cleavable bonds under physiological conditions. "Biodegradableness" refers to material degraded by or in a biological system based on loss of mechanical property. Under certain conditions, the outer shape as well as the dimensions of the implant are preserved during this degradation. If one speaks of a degradation time without adding any additional quantifying information, this refers to the time it takes for the complete loss of the mechanical property. Biostable materials refer to those which remain stable in biological systems and at least partly degrade in same over the long term.

In the case of degradable polymers, there is a differentiation to be made between hydrolytically and enzymatically degradable polymers. Hydrolytic degradation has the advantage that the rate of degradation is independent of the implantation site since water is present everywhere. In contrast, local enzyme concentrations differ greatly. With biodegradable polymers or materials, degradation thus ensues from pure hydrolysis, enzymatically-induced reactions or through a combination of the two. Typical hydrolyzable chemical bonds are amide, esterase or acetal bonds. When degrading, two mechanisms can be observed. With surface degradation, the hydrolysis of chemical bonds occurs solely on the surface. Due to its hydrophobic nature, polymer degradation occurs faster than the water diffusion inside the material. This mechanism is above all observed with poly(anhydride)s or poly(orthoester)s. For the poly(hydroxy carboxylic acid)s such as poly(lactic acid)s or poly(glucose acid)s, the corresponding copolymers respectively, which are of predominant importance for the shape-memory effect, the entire volume of the polymer will degrade. The element determining the rate is hereby the hydrolytic bond cleavage since water diffusion occurs relatively quickly in the rather hydrophilic polymer matrix. Crucial to the use of biodegradable polymers is that, on the one hand, the degradation rate be controlled or variable and, on the other, that the products of degradation are non-toxic.

The invention claims all the afore-mentioned biodegradable shape-memory polymers.

It is particularly preferred in one development of the inventive occlusion device to have the braiding of the occlusion device taper to the diameter of a catheter to be used in the minimally-invasive surgical procedure. The advantage to this embodiment is in particular to be seen in that the catheter system used for implantation and explanation can have a considerably reduced inner diameter, which above all significantly increases maneuverability of the occlusion device to be implanted. This thus improves the accuracy when positioning the device in the defect to be occluded. In the case of an occluder made from nitinol, the inner diameter of the catheter to be used during implantation or explanation ranges between 8 to 10 Frenches, whereas in the case of occlusion devices made from polymer synthetics, the inner diameter only need be between 6 and 8 Frenches.

With respect to the latter cited preferred embodiment of the inventive solution according to which the braiding of the occlusion device tapers to the diameter of the catheter used in an intravascular surgical procedure, a further development provides for the proximal retention area of the occlusion device with its proximal wall to be configured such that the proximal wall curves outward upon the occlusion device expanding so as to come into position in such manner with the septal wall. This reflects a particularly simple to realize and thereby effective way to form the proximal wall in the occlusion device. It is thus possible to form the entire occlusion device as one single piece of braiding so that no mechanical connecting elements are needed between the proximal wall and the crosspiece on the one hand and, on the other, the dimensions of the occlusion device in the folded state can be further minimized. Of course, other embodiments for forming the proximal wall at the proximal retention area are just as conceivable here.

So that the inventive occlusion device will exhibit the functionality of retrievability, a preferred further development of the occlusion device provides for the distal retention area to exhibit a holder, preferably arranged axially to the crosspiece, whereby the holder has at least one connecting element engageable with a catheter. With this connecting element, which is preferably arranged on the distal end of the occlusion device such that it does not project over the distal end of the septal wall, preventing the components of the implant from being in continuous contact with the blood, explanting the occlusion device according to this further development becomes a simple process. A connecting element which can engage with a catheter meanwhile facilitates the implanting and positioning of the occlusion device (folded during the implantation procedure) in the septal defect to be occluded. Various different mechanisms are conceivable as connecting elements such as engaging members, for example, or even hooks and/or eyelets which can be force-fit to the corresponding complementary-configured connecting elements of a catheter.

Another advantageous further development provides for the occlusion device to be configured to be reversibly foldable and expandable so that the device in its expanded state can be folded back up again, for example with the aid of an explanation catheter, whereby the force-fit connection between the proximal wall formed at the proximal retention area, the peripheral area of the proximal wall respectively, and the septal wall can be disengaged. It is thereby conceivable during explanation for a catheter to engage with a connecting element at the distal end of the occlusion device for example, with the folding of the occlusion device being effected by external manipulation aided by the catheter. The occlusion device is thus completely reversibly retractable in the catheter, which enables the complete removal of the device.

The method according to the invention affords the prospect of realizing a particularly simple manufacturing of the occlusion device described above. First, a ball-shaped or bag-shaped hollow braiding is formed, using for example a round braiding machine as has already been described in the WO 2005/020822 A1 patent application. However, a special braiding head is necessary to do so, which will be described in greater detail below with reference to the figures. The technology used in particular here is one in which the configured braiding is bundled at the trailing end of the length of the braiding; i.e., at what will later be the distal end of the occlusion device, while the leading end of the length of the braiding; i.e., what will later be the proximal end of the occlusion device, is closed. It is thereby possible to produce a spherical or bag-like hollow braiding, the bundled end of which corresponds to the distal end of the finished occlusion device and the opposite closed end to the proximal end of the finished occlusion device. The finished occlusion device exhibits mechanical properties in terms of, for example, expansion, stability, strength, etc., which can be custom-adapted to the later use of the occlusion device. In advantageous manner, metallic wires or even organic threads can be incorporated into the braiding.

With respect to the method, it is preferably provided for the process step of forming the retention area and the crosspiece to include a procedural molding and heat treatment step. This is of particular advantage when the ball-shaped hollow braiding formed is made from nitinol or another material which has shape-memory properties or effect. Preferably provided for the inventive occlusion device is forming the braiding from a shape-memory polymer which is based on a polyanhydride matrix or a polyhydroxy-carboxylic acid, for example. These are synthetic degradable materials which have a thermally-induced shape memory effect. Yet other shape-memory polymers such as for example block copolymers would also be conceivable. The essential point is that such materials can be readily and simply brought into their applicable final form using a combination of molding and heat treatment steps. A finished occluder can then be tapered to the dimensions of a catheter, for example. After exiting the catheter, the occlusion device then unfolds by itself and again assumes that profile to the ball-shaped hollow braiding to which the occlusion device was molded during the manufacturing process in the molding and heat treatment step.

It is preferred for the ball-shaped hollow braiding to be manufactured in such a manner that the thin threads or wires constituting the finished braiding intertwine at the proximal end of said braiding when the ball-shaped hollow braiding is formed. This represents a conceivable and especially simple manner of producing an occlusion device in accordance with the present invention, the proximal retention area of which exhibits a closed, flat form to the proximal end (proximal surface). Of course, other manufacturing methods are naturally also conceivable.

The following will make reference to the drawings in providing a more precise detailing of preferred embodiments of the inventive occlusion device as well as of a round braiding machine to provide clarification of the inventive manufacturing method for the occlusion device by example.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 6 is a detail view of the braiding head of the round braiding machine depicted in FIG. 4;

FIG. 7 is an example of a braiding produced with the braiding head shown in FIG. 6, which can serve as the base structure for the occlusion device according to the present invention;

FIG. 10a is a spherical braiding as a base body for different occlusion devices in accordance with the present invention which is produced with a special braiding method and which exhibits a distal holder;

FIG. 10b is a sectional side view of the right side of an inventive PFO-type occlusion device, whereby the occlusion device is made from a spherical braiding in accordance with FIG. 9a;

FIG. 10c is a sectional side view of the right side of an inventive ASD-type occlusion device, whereby the occlusion device is made from a spherical braiding in accordance with FIG. 9a;

FIG. 11 is a sectional side view of the right side of an inventive PFO-type occlusion device, whereby the occlusion device is made from a ball-shaped, bulb-shaped or teardrop-shaped base braiding structure in accordance with FIGS. 9a-9c and comprises a distal holder;

FIG. 12 is a sectional side view of the right side of an inventive VSD-type occlusion device, whereby the occlusion device is made from a ball-shaped, bulb-shaped or teardrop-shaped base braiding structure in accordance with FIGS. 9a-9c and comprises a distal holder;

FIG. 13 is a sectional side view of the right side of an inventive ASD-type occlusion device according to the invention, whereby the occlusion device is made from a ball-shaped, bulb-shaped or teardrop-shaped base braiding structure in accordance with FIGS. 9a-9c and comprises a distal holder;

FIG. 14 is a sectional side view of the right side of an inventive PDA-type occlusion device, whereby the occlusion device is made from a ball-shaped, bulb-shaped or teardrop-shaped base braiding structure in accordance with FIGS. 9a-9c and comprises a distal holder;

FIG. 15b is a sectional side view of the right side of a PFO-type occlusion device known from the prior art, for example in accordance with U.S. Pat. No. 5,725,552, whereby the occlusion device is made from a tubular braiding in accordance with FIG. 15a;

FIG. 15c is a sectional side view of the right side of an ASD-type occlusion device known from the prior art, for example in accordance with U.S. Pat. No. 5,725,552, whereby the occlusion device is made from a tubular braiding in accordance with FIG. 15a;

FIG. 16b is a sectional side view of the right side of a PFO-type occlusion device known from the prior art, for example in accordance with WO 2005/020822 A1, whereby the occlusion device is made from a tubular braiding in accordance with FIG. 16a; and FIG. 16c is a sectional side view of the right side of an ASD-type occlusion device known from the prior art, for example in accordance with WO 2005/020822 A1, whereby the occlusion device is made from a tubular braiding in accordance with FIG. 16a.

DESCRIPTION OF EMBODIMENTS

Figure 1:
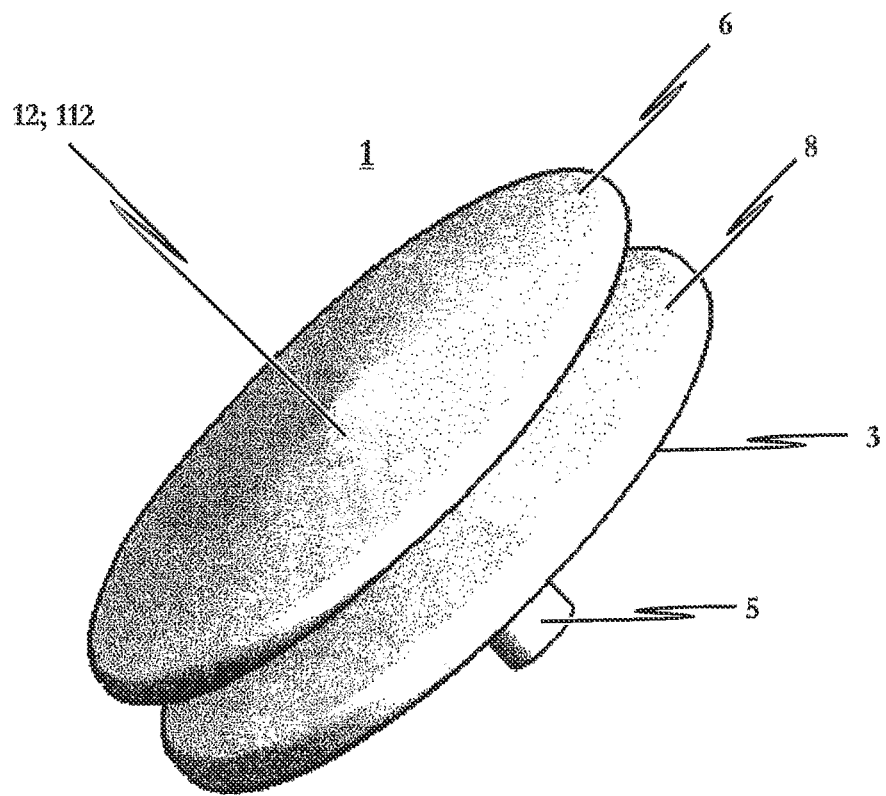
FIG. 1 is a perspective view of a preferred first embodiment of an occlusion device according to the present invention in expanded state in which only the outlined contour of the occlusion device is depicted.
Figure 2:
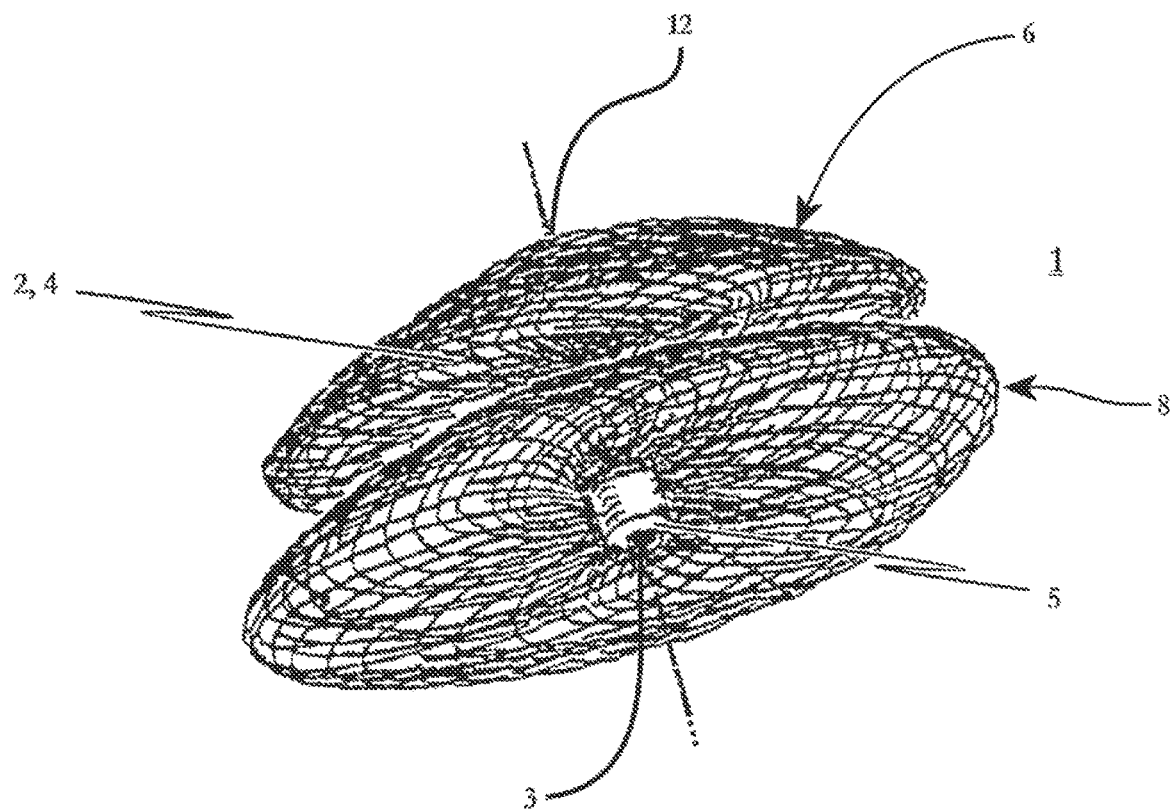
FIG. 2 is a perspective detail view of the distal retention area of the first embodiment of the FIG. 1 occlusion device in the expanded state.
Figure 3:
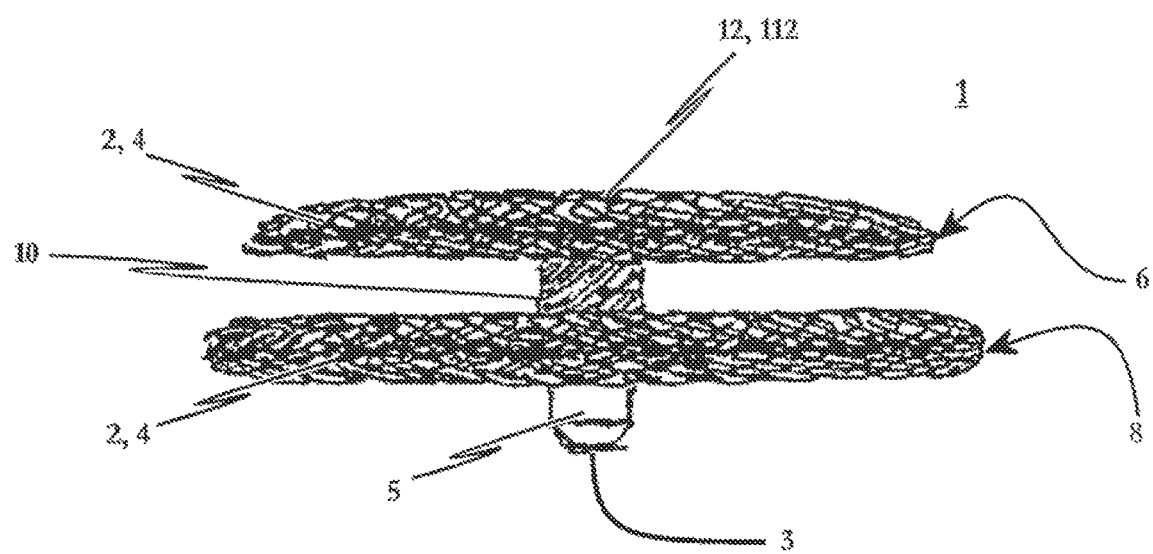
FIG. 3 is a side view of the inventive occlusion device shown in FIG. 2 in the expanded state.

FIG. 1 shows a perspective view of a preferred first embodiment of the occlusion device 1 according to the invention in the expanded state, whereby only the outlined contour of occlusion device 1 is depicted in FIG. 1. FIG. 2 shows a perspective detail view of the distal retention area 8 of the first embodiment of the occlusion device 1 shown in the expanded state in FIG. 1. FIG. 3 shows a side view of the inventive occlusion device 1 shown in expanded state in FIG. 2.

The occlusion device 1 essentially consists of a braiding 2 of thin wires or threads 4, preferable made from nitinol or another shape-memory material or material having memory effect. The braiding 2 exhibits sufficient flexibility such that the occlusion device 1 can be tapered to the diameter of a (not explicitly shown) catheter used in an intravascular surgical procedure. Because of the material's memory effect, the occlusion device 1 tapered as such has a shape-memory function such that the device 1 self-expands after exiting the catheter and reassumes the predefined form which corresponds to its use. This normally ensues after the occlusive device 1 initially disposed in the catheter has been positioned at the location to be treated.

As especially shown in FIGS. 2 and 3, the occlusion device 1 exhibits a proximal retention area 6, a distal retention area 8 and a cylindrical crosspiece 10 arranged between said proximal and distal retention areas 6, 8 in the expanded state. The two retention areas 6, 8 serve to occlude a defect or shunt in a septum. This ensues by areas 6, 8 positioning against the two sides of the shunt to be occluded while the crosspiece 10 passes through the shunt. The occlusion device 1 according to the invention therefore represents an occluding system which can be introduced into a patient's body and positioned at its intended location in a minimally-invasive procedure; i.e., using a catheter and guide wires, for example.

The design to the inventive occlusion device 1 is thereby based on the principle of having the occlusion device 1 taper to the dimensions of the catheter. After being discharged from the catheter, the retention areas 6, 8 then unfold by themselves, thereby positioning themselves on both sides of the septum. The inventive design moreover reflects the occlusion device 1 being a self-positioning and self-centering system. The crosspiece 10 thereby has the length of the atrial diaphragm, the septum respectively, in order to ensure secure placement of retention areas 6, 8 at the septum wall.

Unlike conventional occlusion systems known from the prior art in which a self-expanding umbrella serves as proximal retention area 6, the proximal retention area 6 of the present invention has a flat covering in the form of a proximal wall 112 closed to the proximal end 12 such that no material of the implanted occlusion device 1 whatsoever can extend past the septum wall in the proximal area of the patient's organ. The closed contouring to the proximal end 12 of proximal retention area 6 further ensures that the rim of proximal retention area 6 will always lie flush with the septum wall. This occurs over a relatively wide area independent of the diameter to the defect or the thickness of the atrial diaphragm, the septum respectively, and thereby allows complete endothelialization to occur relatively quickly after the occlusion device 1 has been implanted and precludes any possible defense mechanism reactions from the patient's body since the blood is effectively prevented from coming into contact with the material of implant 1.

Because of the self-expanding property to implant 1 based on the memory effect of the material used, the occlusion device 1 according to the invention exhibits a self-centering function in the shunt or the septal defect. The occlusion device 1 can furthermore be retracted at any time up to the uncoupling of the guide wires of the insertion instrument.

The occlusion device 1 according to the invention can of course furthermore comprise fabric inserts, which are not explicitly shown in the present drawings, the principle behind which is known from the prior art. Such fabric inserts consist mostly of Dacron material. Chemically speaking, Dacron is a polyethylene terephthalate polyester, obtained by polycondensating ethylene glycol and terephthalic acid—dimethyl ester. It is hereby conceivable to incorporate the fabric inserts within the interior of crosspiece 10 or at the proximal end 12 of retention area 6 in order to be able to fully occlude the defect or the shunt in the septum wall. The fabric inserts can be incorporated by bracing same within occlusion device 1, for example. The implant 1 inserted into the body will then be completely enveloped by the body's own tissue within a few weeks or months.

The braiding 2 which serves as the base structure for the occlusion device 1 according to the invention exhibits sufficient rigidity to clamp the fabric insert and have it remain in position.

The braiding 2 converges into a holder 5 at the distal end 3 of distal retention area 8. This is thereby realized by producing an internal thread in holder 5 which then serves to engage with a guide wire of a not shown insertion instrument when the occlusion device 1 is being guided to the appropriate position relative the location of the defect in the septum, for example in an intravascular surgical procedure. After the occlusion device 1 has been positioned in the shunt or defect, the engagement between the guide wire of the insertion instrument and distal end 3 is then disengaged. It is, of course, also conceivable to make use of a differently-configured mechanism in place of an internal thread in holder 5 at distal end 3.

As already indicated, FIG. 1 shows a perspective view of the preferred first embodiment of the occlusion device 1 according to the invention in expanded state while FIG. 2 shows a perspective partial view of the distal retention area 8 of the occlusion device 1 shown in FIG. 1. For simplification purposes, FIG. 1 only shows the outline of occlusion device 1. For even further simplification, a detailed depiction of the braiding 2 serving as the base structure is dispensed with and the form of occlusion device 1 is shown as that of a closed surface. This occlusion device 1 exhibits a much flatter proximal retention area 6 compared to the first embodiment. Depending upon actual intended application, the proximal retention area 6 is configured in a more or less distinctly flattened shape so as to ultimately form the proximal wall 112 in the expanded state. Yet also conceivable would be for the proximal wall 112 to exhibit a completely flattened spherical shape or an almost plate-shaped profile.

Figure 4:
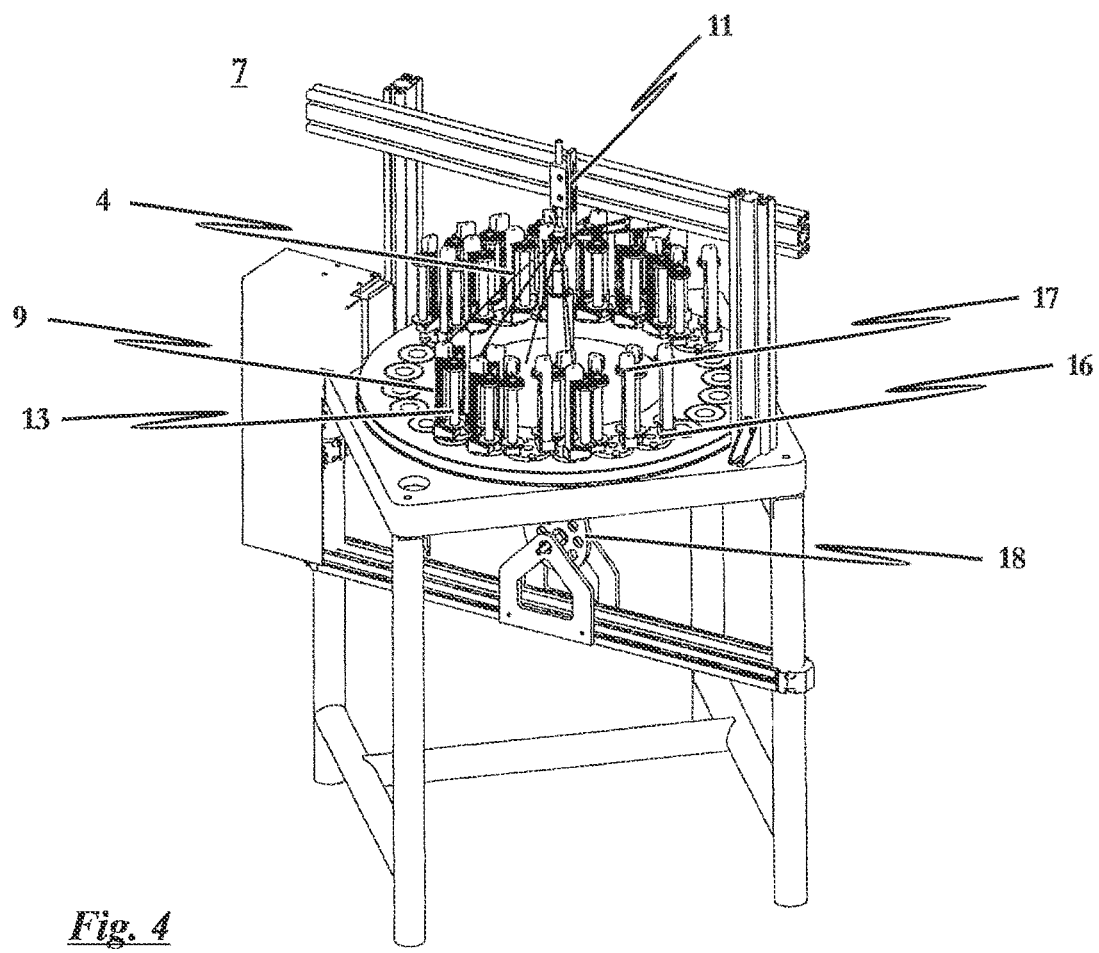
FIG. 4 is a three-dimensional view of a round braiding machine to illustrate the inventive manufacturing method for the occlusion device.
Figure 5:
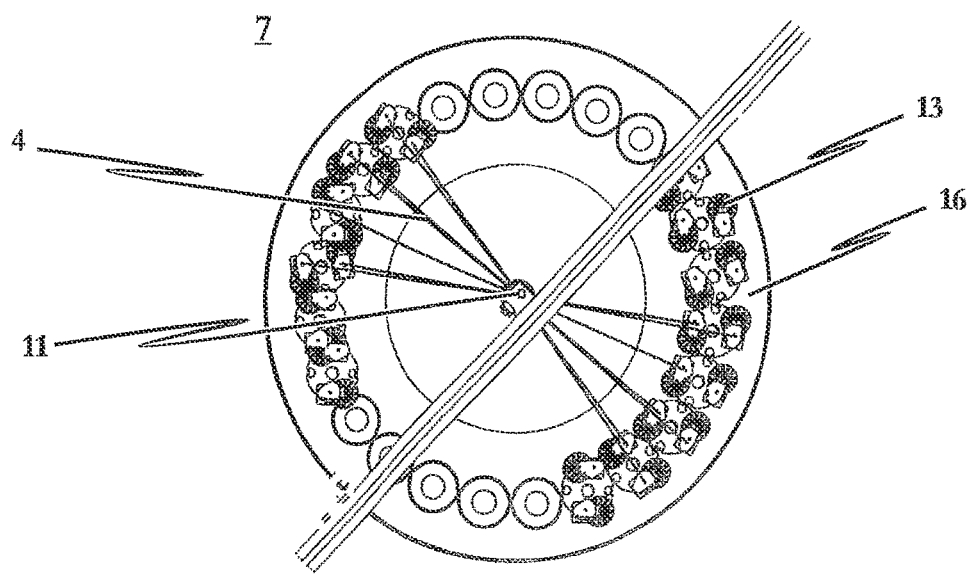
FIG. 5 is a top plan view onto the round braiding machine depicted in FIG. 4 to illustrate the inventive manufacturing method for a ball-shaped, bulb-shaped or teardrop-shaped base braiding structure in accordance with FIGS. 9*a*-9*c*, which can serve as a base structure for the occlusion device according to the present invention.
Figure 8A:
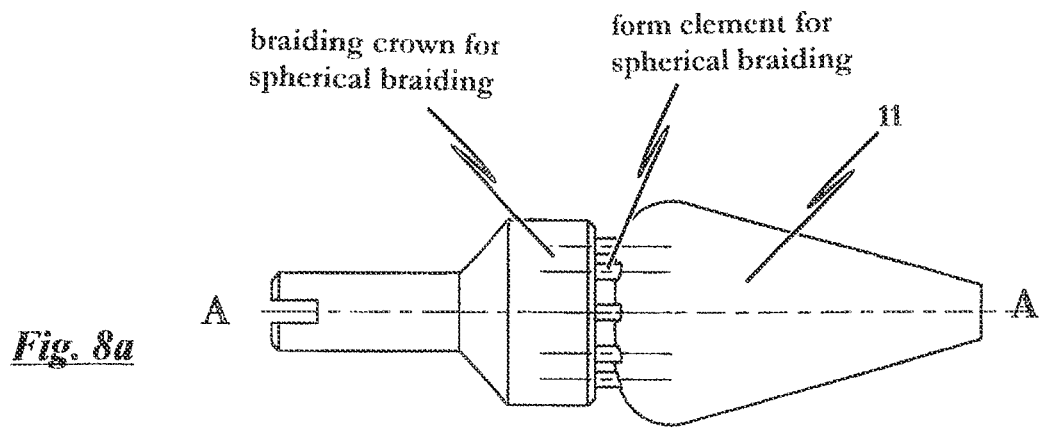
FIG. 8*a* is a side view of a special braiding head for manufacturing a ball-shaped, bulb-shaped or teardrop-shaped base braiding structure in accordance with FIGS. 9*a*-9*c*, which can serve as the base structure for the occlusion device according to the present invention.
Figure 8B:
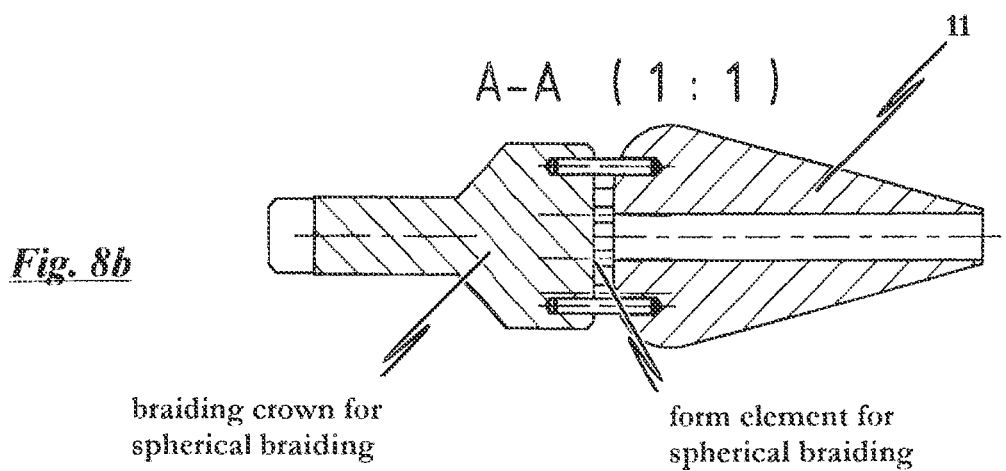
FIG. 8*b* is a sectional view of the braiding head according to FIG. 8*a*.
Figure 8C:
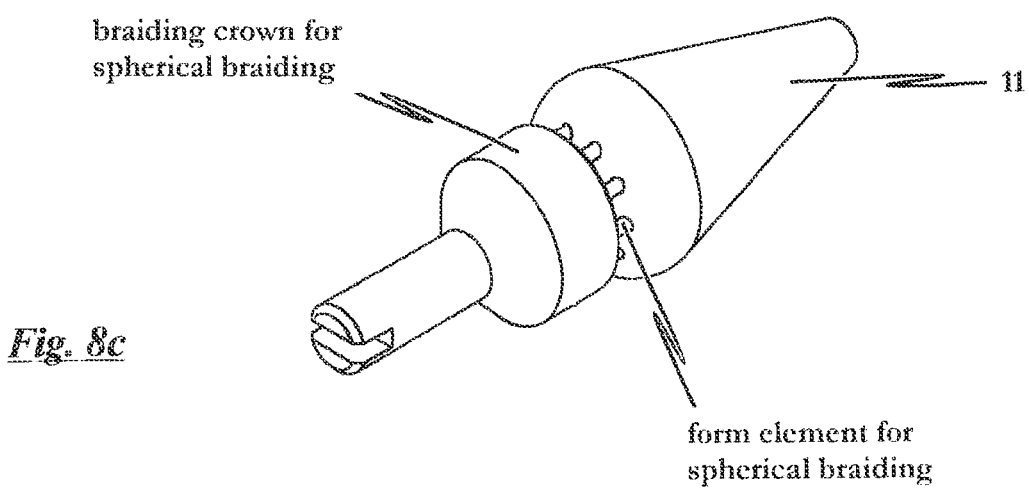
FIG. 8c is a stereoscopic representation of the special braiding head used to produce a spherical braiding.
Figure 9A:
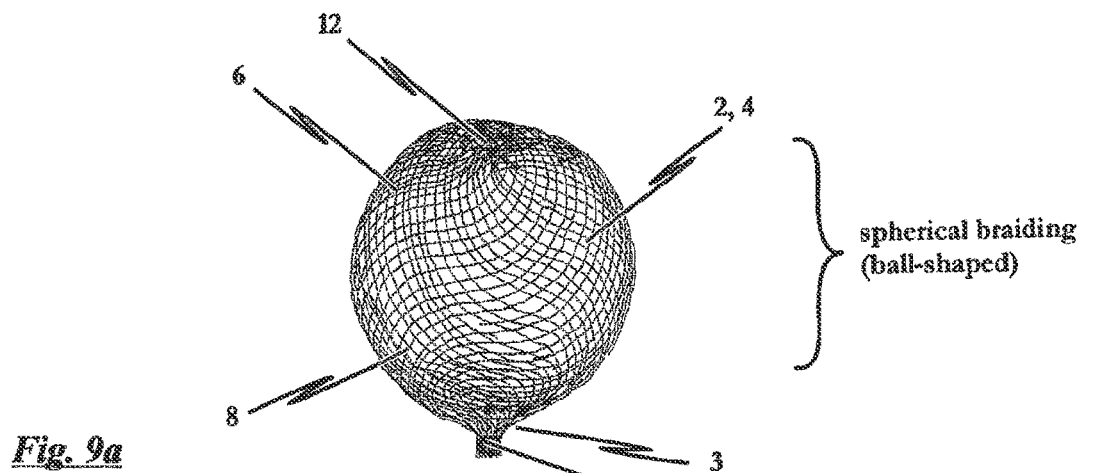
FIG. 9a is a perspective representation of a base body for a spherical braiding constituting the initial body for the inventive occlusion device, whereby the base body is configured in a form as close to a ball as possible.
Figure 9B:
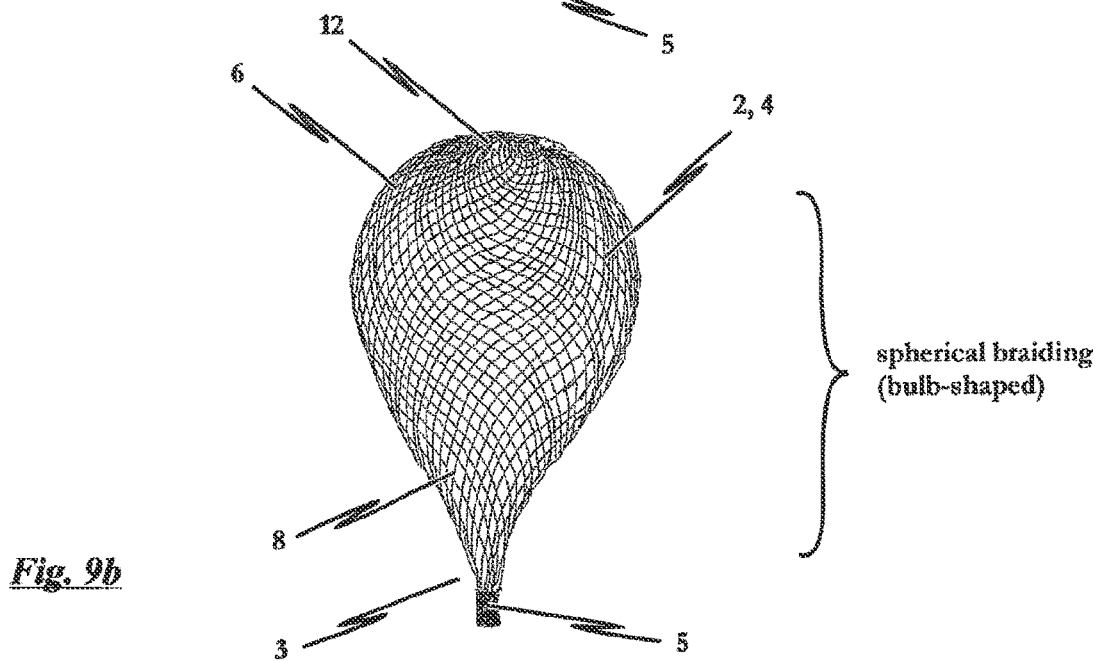
FIG. 9b is a perspective representation of a base body for a spherical braiding suited for producing the occlusion device according to the present invention and whereby the base body is configured to the greatest extent possible in the form of a bulb-shaped body.
Figure 9C:
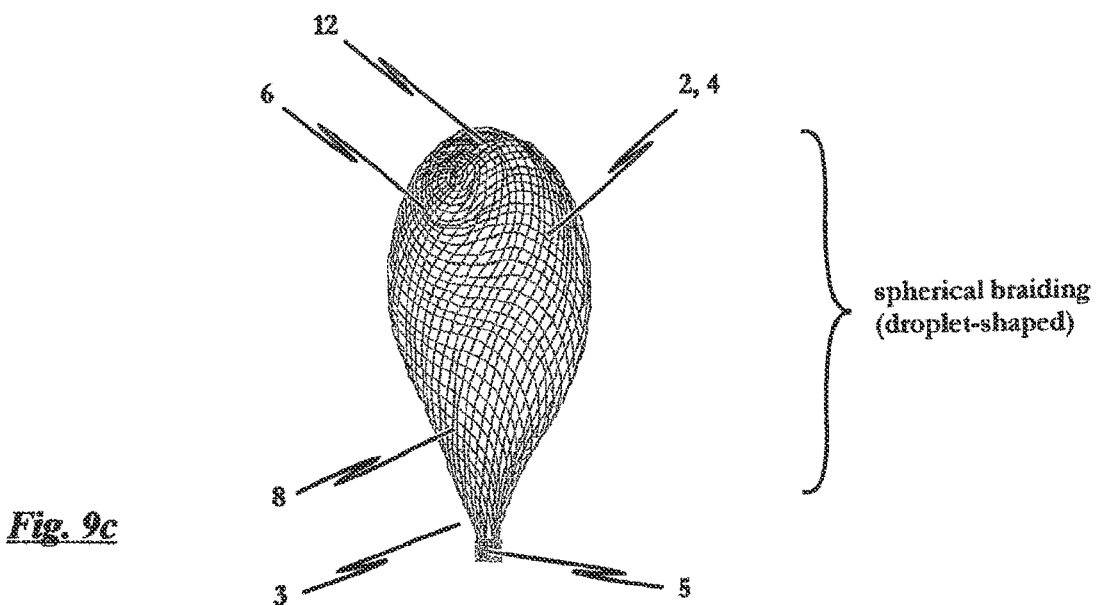
FIG. 9c is a perspective representation of a base body for a spherical braiding, whereby the base body is suited for producing the occlusion device according to the present invention and whereby the base body is configured in a teardrop-shaped form.
Figure 15A:
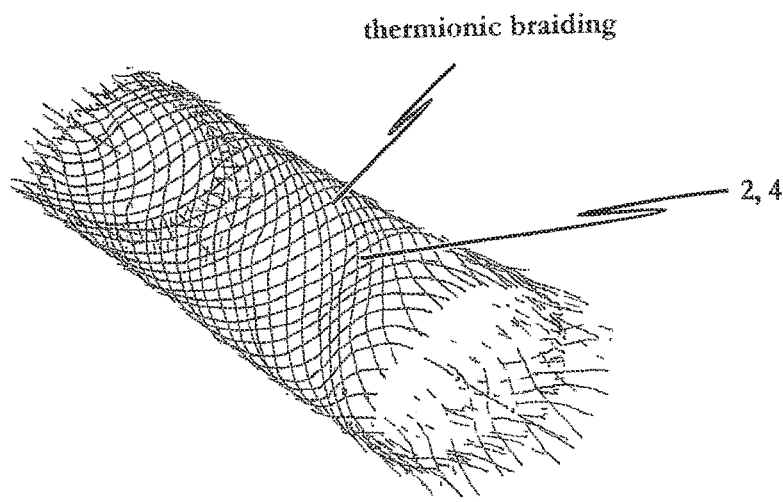
FIG. 15a is a tubular braiding known from the prior art, for example in accordance with U.S. Pat. No. 5,725,552, constituting the starting structure or base for manufacturing a known occlusion device, whereby the respective ends of the tubular braiding need to be held in a holder.
Figure 15B:
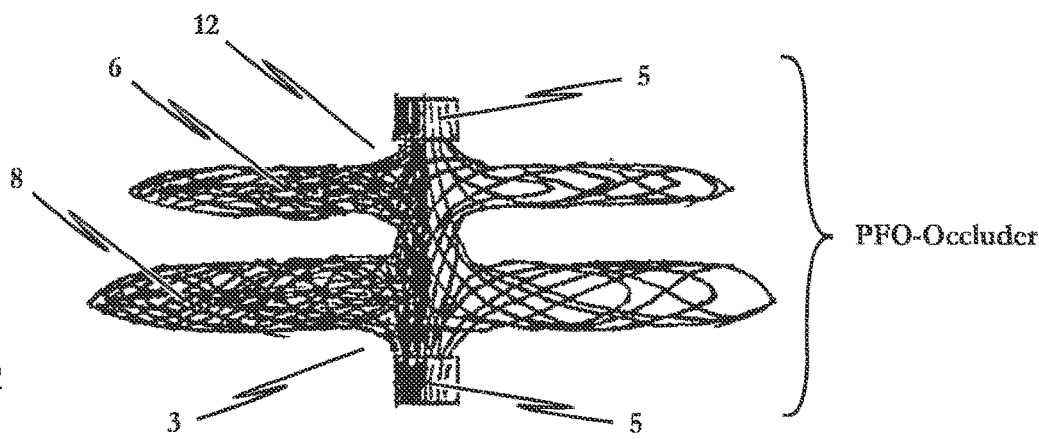
Figure 15C:
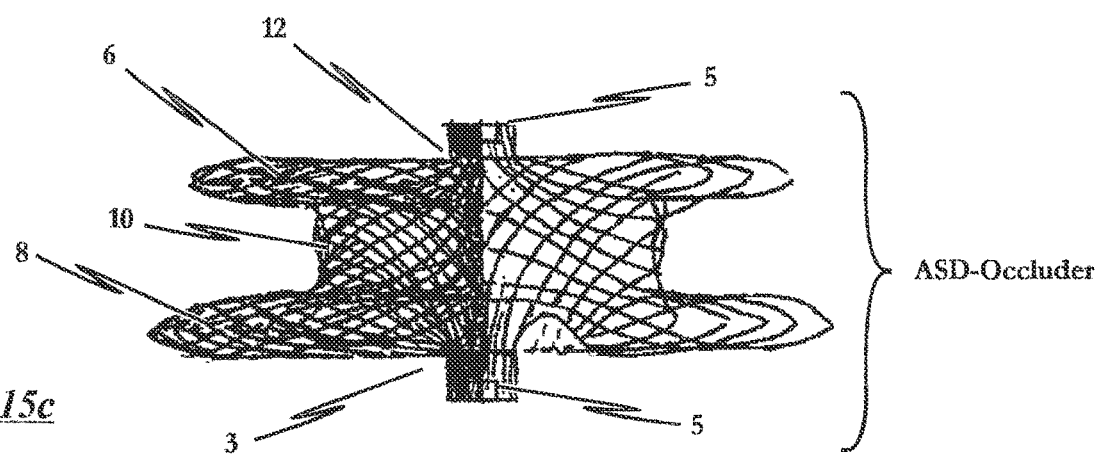
Figure 16A:
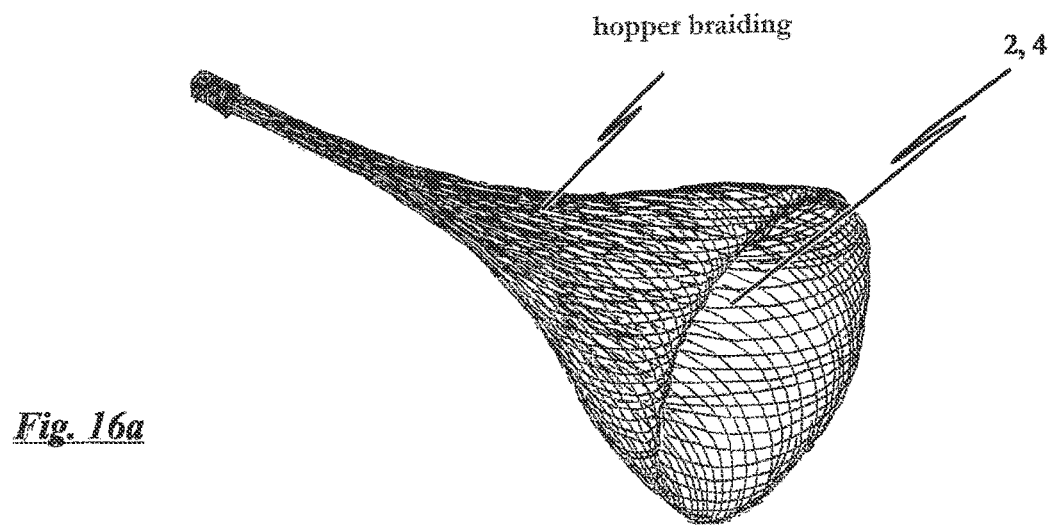
FIG. 16a is a tulip-shaped or bell-shaped braiding having a distal holder as known from the prior art, for example from WO 2005/020822 A1.
Figure 16B:
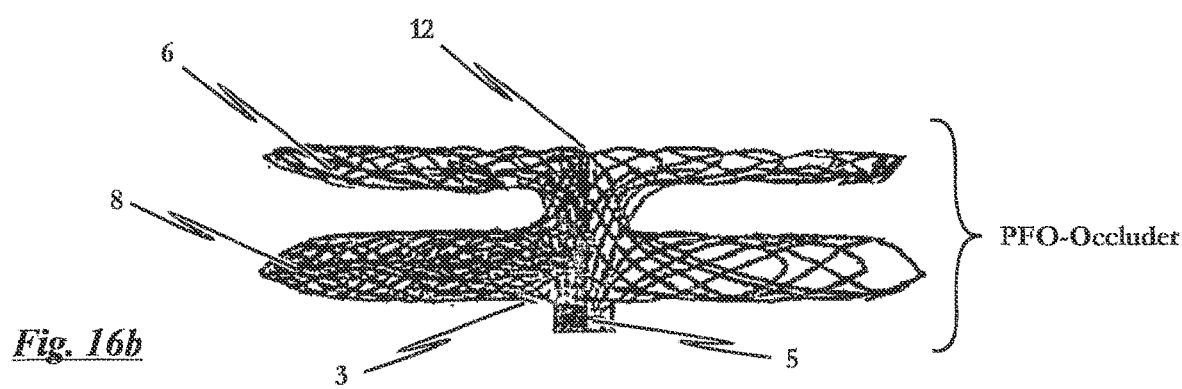
Figure 16C:
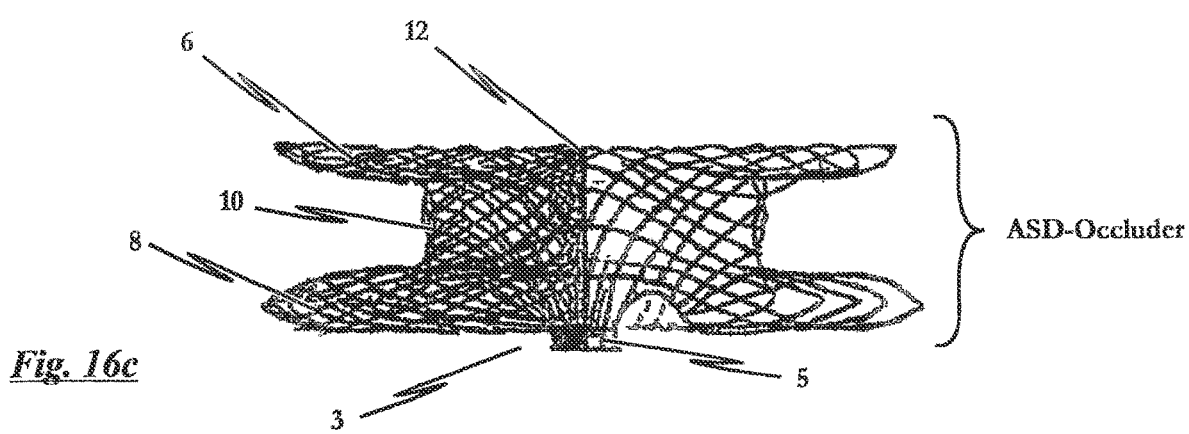

FIG. 4 shows a three-dimensional view of a round braiding machine 7 in order to illustrate the method of manufacturing the occlusion device 1 according to the present invention. FIG. 5 is a top plan view of the round braiding machine 7 depicted in FIG. 4 in order to illustrate the inventive manufacturing method for a ball-shaped, bulb-shaped or teardrop shaped initial braiding structure 2 according to FIGS. 9a-9c, which can serve as the starting structure for the occlusion device 1 according to the invention. FIG. 6 further shows a braiding head 11 for the round braiding machine 7 of FIG. 4 in greater detail, while FIG. 7 shows a braiding 2 made for example with the braiding head 11 shown in FIG. 6, which can serve as the base structure for the occlusion device 1 according to the invention. FIG. 8a is furthermore a side view of a special braiding head 11 for manufacturing a ball shaped, bulb-shaped or teardrop-shaped initial braiding 2 according to FIGS. 9a-9c, which likewise can serve as the base structure for the inventive occlusion device 1. The braiding head 11 according to FIG. 8a is further shown in sectional view in FIG. 8b, while FIG. 8c depicts a stereoscopic representation of the special braiding head 11 for manufacturing a spherical braiding of this type.

In contrast to the known braiding methods where all the threads or wires 4 are gathered into one bundle at the leading end of the braiding 2 and stretched to an extractor device, in the method according to the invention, the material supply is stretched from every second spool 9 to a braiding head 11 and from there to each next respective spool 13 or a multiple of the dividing gap. The spools 13 not having a material supply only have an auxiliary thread extending at least to braiding head 11. The end of the material supply is connected to the end of the auxiliary thread as close as possible to the auxiliary thread spool by means of bolt 14.

The braiding head 11, depicted in detail in the latter cited figures, is of crown-shaped configuration and is provided with form elements 15 which allow the threads or wires 4 to be hooked. Form elements 15 can be lowered in order to hook/unhook braiding 2. Braiding head 11 is axially positioned at the center of the orbit of impellers 16 such that the threads or wires 4 are aligned at a flat downward angle to bobbins 17 of the braiding machine 7.

After all the wires 4 required for the braiding 2 have been joined and tightened, braiding commences in conventionally known manner in that impellers 16 rotate around the center while bobbins 17 shift from impeller to impeller, their orbits thereby crossing. The infeed for braiding 2 is realized by means of a cam plate 18 based on the revolutions of impellers 16. The length to the braiding which can be produced with this method is proportional to the circumference and pitch of braiding 2 as well as to the length of the end of the wire or thread connected to the auxiliary thread. Subsequent braiding, the free ends are bundled or gathered, lopped off from the material supply and uncoupled from the auxiliary thread. The ball-shaped or bag-like hollow braiding 2 thus produced is closed at its leading end and bundled at its trailing end. The wire bundle is gathered such that an internal thread can be produced therein for engaging with the guide wire of a insertion instrument.

In the subsequent material-dependent molding and heat treatment process, the braiding 2 is brought into the form desired for occlusion device 1. The initial structure is suitable for manufacturing an occlusion device 1 for the treatment of a patent foramen ovale (PFO), ventricular septal defect (VSD), atrial septal defect (ASD) or persistent ductus arteriosus (PDA).

It is noted at this point that FIG. 10b, for example, shows a side sectional view of the right side of an inventive PFO-type occlusion device 1, whereby this PFO-occlusion device 1 is made from a spherical braiding 2 as described above. FIG. 10c moreover shows a side sectional view of the right side of an inventive ASD-type occlusion device 1, whereby this ASD-occlusion device 1 as well is made from a spherical braiding 2, the manufacture of which is described above. FIG. 11 furthermore shows another side view of an inventive PFO-type of occlusion device 1.

It is furthermore pointed out that FIG. 12 discloses a side sectional view of the right side of an inventive VSD-type occlusion device 1, whereby this VSD-occlusion device 1 is made from a ball-shaped, bulb-shaped or teardrop-shaped initial braiding 2 as described above. Finally, reference is made to FIGS. 13 and 14 which respectively depict sectional views of the right sides of occlusion devices 1 of the ASD and PDA types. The inventive occlusion devices shown in FIGS. 13 and 14 are in turn made from a ball-shaped, bulb-shaped or teardrop-shaped initial braiding structure in accordance with FIGS. 9a-9c, whereby said initial braiding is produced as described above.

From the perspective of holder 5 and depending upon configuration, an expanded diameter (i.e. distal retention area 8) is formed, followed by crosspiece 10, to which another expanded closed diameter (i.e. proximal retention area 6, proximal wall 112 respectively) is joined. Since circumstances dictate that braiding 2 serving as the base for the occlusion device 1 cannot as such always fully occlude a defect, fabric inserts can be introduced into crosspiece 10 and in the expanding diameters—distal and/or proximal retention areas 6, 8. These fabric inserts, preferably of Dacron, then close the gaps remaining in braiding 2 when occlusion device 1 is in its inserted state. Said fabric inserts can be secured for example by being stretched over the proximal opening like a cloth.

Reference is herewith again made to FIG. 6 which depicts the braiding head 11 of the round braiding machine 7 from FIG. 4 in greater detail, while FIG. 7 shows an example of a braiding 2 produced with the braiding head 11 shown in FIG. 6, which can serve as the starting structure for the occlusion device 1 according to the invention. Clearly to be seen here is that the braiding 2 serving as the base structure for occlusion device 1 is configured in the form of a tubular or bag-shaped braiding 2 closed to it top which only needs to be provided with one holder 5 at its end 3, while the threads or wires 4 on the opposite side 12 are, for example, intertwined from the center outward.

The closed braiding 2 can be shaped as a ball (cf. FIG. 9a), a bulb (cf. FIG. 9b) or also a teardrop (cf. FIG. 9c), whereby only one holder 5 having an internal thread for snugly connecting with an insertion catheter is provided at distal end 3.

The core but also highly specific occlusion device 1 can be manufactured from the ball shaped (FIG. 9a), bulb-shaped (FIG. 9b) or teardrop-shaped (FIG. 9c) initial braiding structure 2, as will be described below, whereby this inventive occlusion device 1 can be given substantially improved functional properties such as in particular the extreme flattened form to the proximal wall 112 and without any additional seams in proximal retention area 6, proximal wall 112 respectively.

Specifically, this is an occluder 1 for treating an atrial septal defect (ASD), which is a hole in the heart's atrial septum. FIG. 13 shows an example of such an ASD-occluder 1.

Occluder 1 can moreover be produced to treat a patent foramen ovale (PFO); i.e. for treating oval openings/apertures in the heart's atrial septum. FIG. 11 shows this type of inventive PFO-occluder.

It is moreover conceivable in accordance with the invention, to manufacture an occluder to treat persistent ductus arteriosus (PDA), meaning to treat an open channel between the aorta and the pulmonary artery. FIG. 14 depicts this type of PDA-occluder 1.

It is also pointed out in conclusion that, according to the invention, an occluder 1 for treating a ventricular septal defect (VSD) is also conceivable; i.e. for treating a hole in the heart's ventricular wall. FIG. 12 shows an example of such a VSD-occluder.

Attention is drawn to the fact that realizing the invention is not limited to the embodiments specified by the figures, but is instead feasible in a plurality of variants.

What is claimed is:

1. A braiding machine producing a spherical braid structure, the braiding machine comprising:
    a braiding head unit comprising in combination:
    a braiding head,
    a braiding crown for spherical braiding,
    a plurality of form elements,
    the braiding head having a first end located proximal to the braiding crown and an opposite second end,
    the first end being curved or rounded peripherally in a direction from the first end to the second end,
    wherein the braiding head unit is placed axially in a center of an orbit of impellers of the braiding machine, and each of said impellers arranged to hold an end of a wire extending from a position between the braiding crown and across the braiding head of the braiding head unit,
    wherein the form elements comprise a plurality of elongate elements which connect the braiding crown to the braiding head, thereby forming a gap between the braiding crown and the braiding head, so that when in use, wires of a ball braid between the braiding crown and the braiding head, and stretch past the form elements.

2. The braiding machine according to claim 1, wherein the braiding crown has a circular shape at an end connected to the braiding head, said plurality of elongate elements being disposed about a periphery of said circular shape.

3. The braiding machine according to claim 1, wherein the elongate elements are connected to a perimeter of the first end of the braiding head, the first end being curved or rounded radially outside the perimeter.

* * * * *